(12) United States Patent
Young

(10) Patent No.: US 10,492,998 B2
(45) Date of Patent: Dec. 3, 2019

(54) TRANSNASAL TUBE

(71) Applicant: Venner Medical Technologies SA, Mahe (SC)

(72) Inventor: Peter J. Young, King's Lynn (GB)

(73) Assignee: Venner Medical Technologies SA, Mahe (SC)

(*) Notice: Subject to any disclaimer, the term of this patent is extended or adjusted under 35 U.S.C. 154(b) by 0 days.

(21) Appl. No.: 15/558,595

(22) PCT Filed: Mar. 17, 2016

(86) PCT No.: PCT/GB2016/000054
§ 371 (c)(1),
(2) Date: Sep. 15, 2017

(87) PCT Pub. No.: WO2016/146965
PCT Pub. Date: Sep. 22, 2016

(65) Prior Publication Data
US 2018/0078462 A1    Mar. 22, 2018

(30) Foreign Application Priority Data

Mar. 17, 2015   (GB) .................................. 1504481.1

(51) Int. Cl.
*A61J 15/00* (2006.01)
*A61M 25/02* (2006.01)

(52) U.S. Cl.
CPC ......... *A61J 15/0034* (2013.01); *A61J 15/003* (2013.01); *A61J 15/0003* (2013.01); *A61J 15/0026* (2013.01); A61M 2025/0226 (2013.01)

(58) Field of Classification Search
CPC .. A61J 15/003; A61J 15/0034; A61J 15/0026; A61M 2025/0226
See application file for complete search history.

(56) References Cited

U.S. PATENT DOCUMENTS

| | | | | |
|---|---|---|---|---|
| 4,778,448 A * | 10/1988 | Meer | ..................... | A61J 15/003 128/207.18 |
| 2005/0236001 A1 | 10/2005 | Williams | | |
| 2009/0292256 A1* | 11/2009 | Cubberly | .............. | A61M 25/02 604/180 |
| 2013/0046172 A1* | 2/2013 | Waitzman | ................ | A61B 5/06 600/424 |
| 2013/0340764 A1* | 12/2013 | Atkinson | .............. | A61M 25/02 128/207.18 |
| 2014/0041666 A1* | 2/2014 | Slaga | ................ | A61M 16/0683 128/207.18 |

FOREIGN PATENT DOCUMENTS

CN         202844308 U      4/2013

OTHER PUBLICATIONS

International Search Report and Written Opinion of the International Searching Authority, dated Jun. 21, 2016, for International Patent Application No. PCT/GB2016/000054.

* cited by examiner

*Primary Examiner* — Imani N Hayman
*Assistant Examiner* — Tiffany Legette
(74) *Attorney, Agent, or Firm* — Morgan, Lewis & Bockius, LLP

(57) ABSTRACT

This invention relates to a transnasal tube assembly comprising a transnasal tube and an integrated tether for anchoring the transnasal tube, wherein the integrated tether is permanently fixed to the transnasal tube at a first fixation point, and wherein the integrated tether is reversibly fixable to the transnasal tube at a second fixation point.

23 Claims, 4 Drawing Sheets

TRANSNASAL TUBE

CROSS-REFERENCE TO RELATED APPLICATIONS

This application is a U.S. National Stage of International Patent Application No. PCT/GB2016/000054, filed Mar. 17, 2016, which claims the benefit of United Kingdom Patent Application No. GB 1504481.1, filed Mar. 17, 2015, each of which is incorporated by reference herein in its entirety.

The present invention relates to a transnasal tube assembly and in particular, to a transnasal tube assembly that prevents accidental removal, and to a method of inserting and/or anchoring the tube assembly.

Nasogastric tubes are typically inserted into the gastrointestinal tract of a patient. Initially, insertion of the tube involves the step of passing the tube into the nostrils of a patient. Such tubes are often required to be maintained in an operative position in patients for an extended period of time. Thus, it is important to ensure that the insertion, positioning and anchoring of such tubes is as comfortable as possible for the patient, and that the tubes are not accidentally removed from the patient.

Nasogastric tube assemblies have been developed to prevent accidental removal of the tube or assembly from a patient. Such nasogastric tube assemblies are often also known as nasal bridle systems. Currently, there are many nasal bridle systems described and many in use which use magnetic or other means of passing a cord or flexible material though a first nostril, around the nasal septum and out of the other nostril of a patient. The two ends of the bridle can be tied or clamped in place outside the nose, and adjacent to the nostril, and also may be clamped to a nasogastric tube by a number of mechanisms thereby securing the tube in place. With current technology, the two ends of the bridle and the nasogastric tube are fixed at a single point normally with a clamp or tape outside of the nose (i.e. at a single external fixation point). A disadvantage of the attachment of the two ends of the bridle to the tube outside of the nose is that this must be done very close to the skin near the nostril to prevent the tube being pulled out by the patient or a carer from a portion of the tube on the distal patient side of the attachment. Even with the bridle attached very close to the nostril, a patient can put a finger up the nostril, hook out the tube and pull it from the stomach. Bridles attached to feeding or other gastric tubes close to the skin of the nose may also cause irritation and/or pressure sores.

For example, Ballantyne (U.S. Pat. No. 5,185,005 (A)) describes an apparatus that is used to anchor a nasogastric tube external to the nose of a patient, the apparatus employing an elongate flexible member which passes through one nostril, around the posterior nasal septum, and out of the other nostril. The two ends of the flexible member, one passing out of each nostril, are attached to a nasogastric tube or are affixed to an anchoring clip, to which also may be anchored a nasogastric tube. Ballantyne also includes reference to an apparatus and method for installing the elongated flexible member through the patient's nose to pass around the nasal septum utilising a pulling cord, one end of which is affixed to a first magnet and the other end of which is affixed to one end of the bridle. The bridle and pulling cord are then slidably inserted through a first installation tool until the magnet is pulled flush against the distal end of said tool. The first magnet is held in place against the distal end of the first installation tool by tension applied to the bridle and pulling cord which extend from the proximal end of said tool. A second installation tool is used which has a second magnet securely attached to its distal end.

Current nasal bridle systems consist of a separate flexible member (for example a magnet on a cord), a receiving member with a magnet on the tip, a fixing clamp or similar and a nasogastric tube. Thus, current nasal bridle systems employ a number of separate components which are required to be used in combination during the anchoring process and there is a desire to reduce the number of parts that are involved in this process.

Thus, there is a need to securely anchor a transnasal tube, such as a nasogastric tube, in a way that prevents or reduces the possibility of a patient removing the tube without the assistance of a medical professional, reduces the possibility of irritation and pressure sores caused by attachment of the tube to the skin of a patient, and which reduces the number of components required during the anchoring of the transnasal tube, thus facilitating the process of anchoring the tube and making the process cheaper than existing methods.

The present invention seeks to ameliorate problems associated with the prior art described above.

According to the invention, there is provided a transnasal tube assembly comprising a transnasal tube and an integrated tether for anchoring the transnasal tube, wherein the integrated tether is permanently fixed to the transnasal tube at a first fixation point, and wherein the integrated tether is reversibly fixable to the transnasal tube at a second fixation point. Thus, the transnasal tube assembly of the present invention provides a secure means of anchoring the transnasal tube in place during use. Another advantage provided by the invention is that the transnasal tube assembly anchors the transnasal tube against undesired movement relative to the patient's nostril and reduces or prevents unwanted removal of the tube from the patient.

Preferably, the transnasal tube comprises a nasogastric tube. In other embodiments, the transnasal tube may comprise a nasojejunal, oesophageal or feeding tube.

Preferably, the integrated tether comprises a flexible member. Preferably, the flexible member is elongate. Advantageously, the use of a flexible member allows for movement of the tether, facilitating the anchoring of the transnasal tube. Typically, the flexible member may comprise a flexible material such as, for example, a tube, tape, ribbon or cable. Preferably, the flexible member comprises a flexible elastomer, fabric or other material chosen for its flexibility, softness, tensile strength and/or non-irritating properties.

It is preferred that the integrated tether comprises a first end and a second end, wherein the first end is provided adjacent to the first fixation point (i.e. the internal fixation point) and the second end is proximal to the second fixation point (i.e. the external fixation point). Preferably, the first end of the tether is secured to the transnasal tube at a position distal to the posterior nasal septum (i.e. inside the patient) and the second end of the tether is secured to the transnasal tube at a position external to the patient.

Preferably, the integrated tether further comprises a retrieving means (also known as engaging means) at a position proximal to the first fixation point (i.e. at a position proximal to the posterior nasal septum when in use). Preferably, the retrieving means (i.e. engaging means) comprises an element to assist in moving the tether to a position wherein the tether is securely anchored in place. Typically, the retrieving means comprises a magnet. In one embodiment, the retrieving means comprises a hook. Advantageously, the provision of a retrieving means at a position proximal to the first fixation point allows for movement of the tether to a position wherein the transnasal tube is securely anchored in place when in use.

Typically, the transnasal tube comprises a recess to accommodate the magnet provided on the tether. Advantageously, the provision of a recess within the transnasal tube reduces the space required to accommodate the magnet. This is especially important due to the small size of the nostrils of a patient.

Preferably, the transnasal tube assembly further comprises a retrieving member. Advantageously, in use, the retrieving member engages with the retrieving means provided on the integrated tether and facilitates the movement of the tether to a position wherein the transnasal tube is anchored in place. Preferably, the retrieving member is sized to be insertable into the nostril of a patient. Preferably, the retrieving member engages with the retrieving means on the integrated tether to assist in pulling the integrated tether to a position wherein the transnasal tube is anchored in place. It is preferred that the retrieving means and retrieving member comprise mutually attractable elements which engage with one another to facilitate movement of the integrated tether to a position wherein it is anchored in place. Preferably, the retrieving means and the retrieving member comprise a magnet. In another embodiment, the retrieving means comprises a hook and the retrieving member comprises a loop, wherein the hook and loop engage with one another to draw the tether to a position wherein the tether is securely anchored in place. In another embodiment, the retrieving means comprises a loop and the retrieving member comprises a hook.

Typically, the retrieving member comprises an introducing stylet, a wire or other intra-luminal member. It is preferred that the retrieving member comprises a magnet. Typically, the magnet is provided at the distal end of the retrieving member. Advantageously, in use, the magnetic retrieving member engages with the magnet provided on the integrated tether and allows for movement of the tether to a position wherein the transnasal tube is anchored in place when in use.

It is preferred that, in use, the magnet provided on the retrieving member couples with the magnet provided on the integrated tether and the retrieving member is then used to pull the second end of the tether to a position exterior to the patient's nostril.

Preferably, the transnasal assembly comprises a magnet integrated into the flexible member to facilitate the drawing forwards of the flexible member through from posterior to the nasal septum through a nostril using a magnetic tipped retrieving member.

Preferably, the magnet is integrated into the flexible member at approximately 7 cm or more from the permanent fixation point to facilitate the drawing forwards of the flexible member through from posterior to the nasal septum through a nostril using a magnetic retrieving member.

Preferably, the magnet is integrated into the flexible member with at least around 7 cm of flexible member between the permanent fixation point on the nasogastric or feeding tube and the magnet.

Preferably, the magnet is integrated into the flexible member with at least around 7 cm of flexible member between the magnet and the free end of the flexible member.

Preferably, the magnet provided on the tether and the magnet provided on the retrieving member are sized to be insertable into a patient's nostrils. Typically, the magnets comprise a ferromagnetic material. In one embodiment, the magnets may comprise permanent magnets, or combinations of permanent magnets and ferromagnetic material.

It is preferred that the magnets comprise a material which provides adequate force to effect the coupling of the magnets within the nostril or nasopharynx of a patient, and to enable both magnets, when magnetically coupled together, to be pulled from the patient's nostril. Preferably, the magnet provided on the tether is placed into close proximity with (i.e. typically substantially adjacent to) the magnet provided on the retrieving member such that the magnets couple by magnetic force. Preferably, the outer surface of the magnet provided on the retrieving member is attracted to the magnet provided on the tether to facilitate coupling of the magnets and movement of the tether to a position outside of the nostrils of the patient, wherein the tether may be secured in position at a second fixation point.

Preferably, in use, the first fixation point is provided at a position distal to the posterior nasal septum of the patient and the second fixation point is provided at a position exterior to the patient's nostril. The provision of the first fixation point at a position distal to the posterior nasal septum of the patient has the advantage that it provides for secure anchoring of the transnasal tube when in use, preventing or reducing the possibility of the patient accidentally removing the transnasal tube.

Preferably, the transnasal tube assembly comprises a clamp to secure the trasnasal tube and tether together at the second fixation point. In one embodiment, the transnasal tube assembly further comprises adhesive tape to secure the transnasal tube and tether together at the second fixation point.

Preferably, the transnasal tube assembly comprises indication means to indicate the position of the transnasal tube and/or tether when inserted within the nostril of a patient. Typically, the indication means comprises a marker.

Preferably, the nasogastric or feeding tube comprises markings on the tube and/or the flexible member, to indicate the distance to the magnet on the flexible member to assist the assessment of the depth of placement of the typically more rigid retrieving member to allow the retrieving member magnet to attach to the magnet on the flexible member.

It is preferred that the nasogastric tube comprises a depression extending along a longitudinal length of the tube proximal to the first fixation point, wherein in use, the depression accommodates the tether.

Preferably, the nasogastric or feeding tube comprises a recess or plurality of recesses within the feeding tube to accommodate part or all of the volume of the magnet which is integrated into the flexible member.

Preferably, a magnet or ferromagnetic material is provided within a recess or plurality of recesses within the feeding tube to accommodate part or all of the volume of the magnet which is integrated into the flexible member.

Preferably, the nasogastric or feeding tube comprises a depression along all or part of its length proximal to the permanent fixation point, to accommodate the volume or part of the volume of the flexible member.

Preferably, the nasogastric or feeding tube comprises an introducing stylet, wire or other intra-luminal member which is magnetic or has a magnet along its length to attract the magnet integrated into the integrated flexible member to assist in locating it into position within a recess or on the external surface of the nasogastric or feeding tube.

In one embodiment, there may be provided a series of nasogastric or feeding tubes in accordance with the first aspect, the tubes being of different lengths defined by the portion proximal to the permanent fixation point and the length of the distal portion which passes through the oesophagus towards the stomach to enable appropriate sizing of the tube length depending on the size of the patient.

Preferably, the nasogastric or feeding tube comprises a clamp to hold the magnet on the flexible member into a recess within the tube wall to form an external fixation point.

According to a second aspect of the invention there is provided method of anchoring a transnasal tube comprising the transnasal tube assembly of the first aspect, the method comprising the steps of:
(i) inserting the transnasal tube assembly along a first nostril of a patient to a position wherein the first fixation point of the integrated tether is distal to the posterior nasal septum;
(ii) inserting a retrieving member into a second nostril and using the retrieving member to draw the second end of the integrated tether through the second nostril to a position outside the patient; and
(iii) securing the transnasal tube and tether together at a second fixation point outside of the patient.

Preferably, the transnasal tube comprises a nasogastric tube. In other embodiments, the transnasal tube may comprise a nasojejunal, oesophageal or feeding tube.

Preferably, step (ii) comprises the use of a magnet provided at the distal end of the retrieving member and a magnet provided on the integrated tether to draw the second end of the tether out of the second nostril of the patient.

Typically, step (iii) comprises the use of a clamp and/or adhesive tape.

Preferably, the tether comprises a flexible member. Preferably, the tether is elongate. Preferably, the flexible member is inserted with the transnasal tube along a first nostril of the patient to a position where the first fixation point is distal to the posterior nasal septum. Preferably, the magnet provided on the integrated tether engages with the magnet provided on the retrieving member and the magnets are placed in close proximity such that they couple with one another. Preferably, the retrieving member is then used to draw the tether through the second nostril of the patient to a position outside the patient. Preferably, the second end of the tether when external to the patient is secured to the transnasal tube at a second fixation point, by means of a clamp, adhesive tape or other securing means.

It is preferred that the position of the transnasal tube and tether is monitored using indication means. Preferably, the indication means is provided in the form of a marker.

According to a third aspect of the invention, there is provided a kit comprising the transnasal tube assembly of the first aspect, further comprising a retrieving member.

Preferably, the retrieving member comprises a magnet at the distal end thereof.

It is preferred that the kit further comprises a clamp and/or adhesive tape for securing the transnasal tube and tether at the second fixation point.

The invention will now be described by way of example, with reference to the accompanying drawings, in which.

Figure 3:
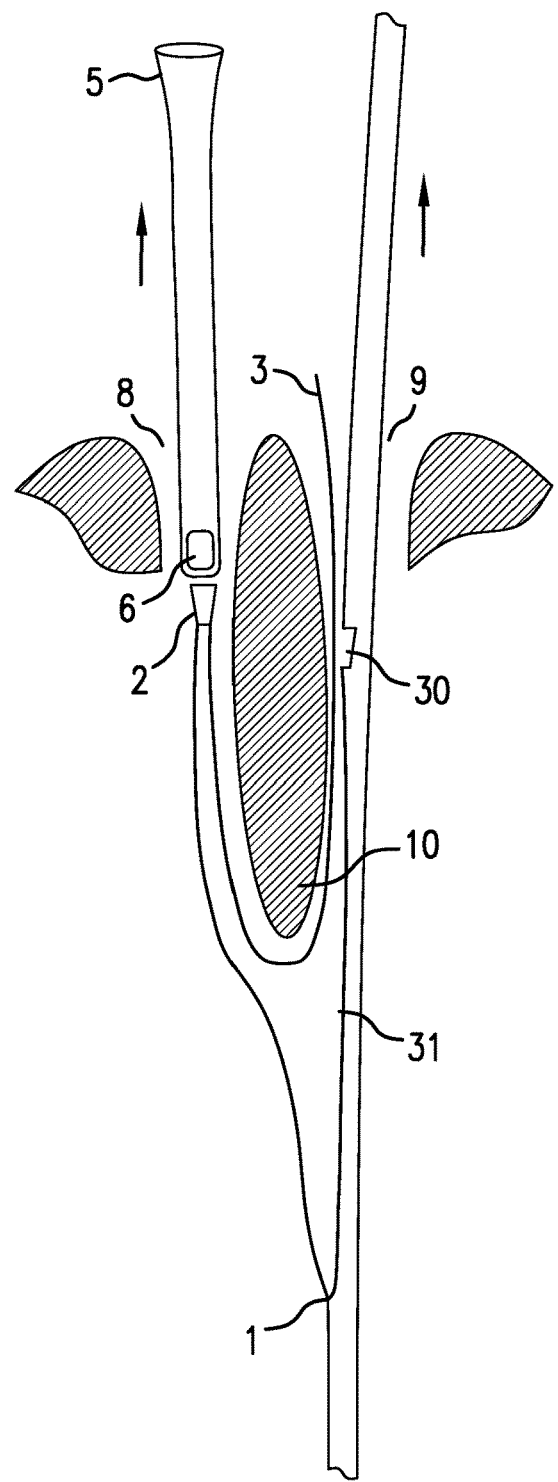
Figure 4:
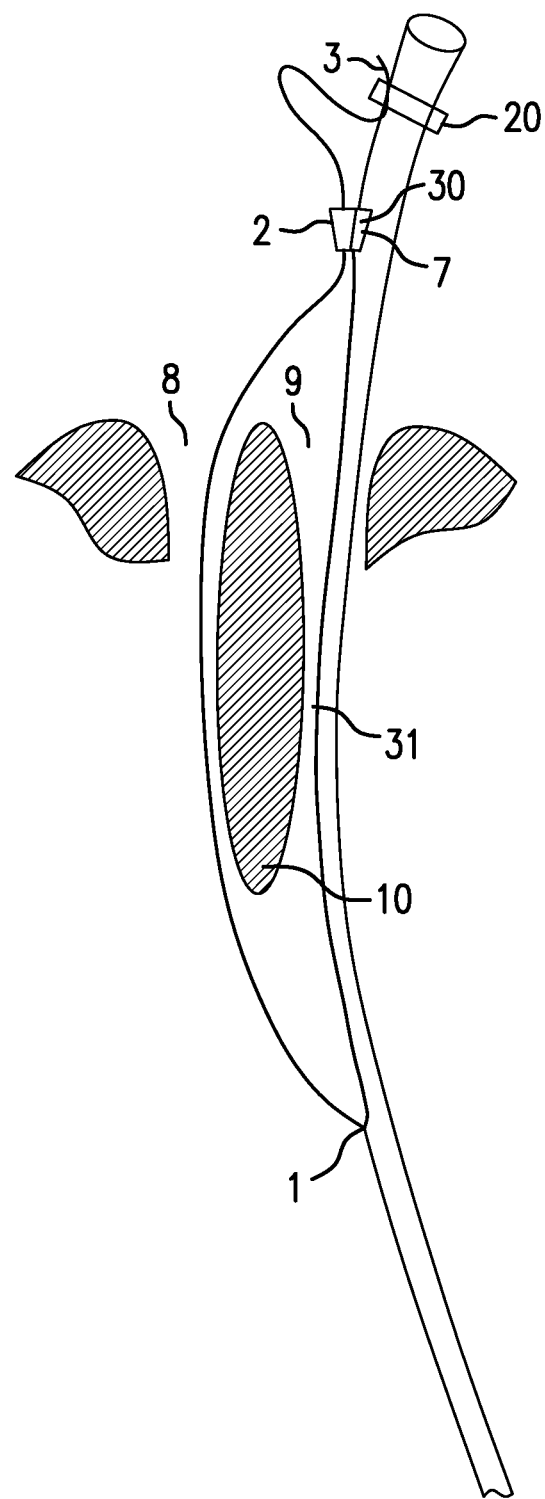

FIG. 3 is a schematic view of the transnasal tube assembly and retrieving member according to the invention during the process in which the transnasal tube is anchored in position when in use; and FIG. 4 is a schematic view of the transnasal tube assembly according to the invention in the anchored configuration, wherein the integrated tether is attached to the transnasal tube at the first and second fixation points.

Referring to the drawings, there is illustrated a transnasal tube assembly 12 comprising a transnasal tube 14 and an integrated tether 16 for anchoring the transnasal tube 14, wherein the integrated tether 16 is permanently fixed to the transnasal tube 14 at a first fixation point 1, and wherein the integrated tether 16 is reversibly fixable to the transnasal tube 14 at a second fixation point 7. The first fixation point is also referred to as the internal fixation point and the second fixation point 7 is also referred to as the external fixation point.

FIGS. 1 to 4 show schematic representations of a transnasal tube wherein the width of the proximal end (i.e. the end external to the patient when in use) is slightly larger than that of the distal end (i.e. the end inserted into the patient when in use). The skilled person would understand that nasogastric tubes having different dimensions to those shown in the drawings could be used in accordance with the invention, such as a nasogastric tube having substantially the same width at the distal end and the proximal end of the tube.

In this embodiment, the transnasal tube 14 comprises a nasogastric tube and the tether 16 comprises a flexible member. The flexible member 16 is elongate and comprises a flexible material such as, for example, a tube, tape, ribbon or cable. The flexible member 16 comprises a flexible elastomer, fabric or other material chosen for its flexibility, softness, tensile strength and/or non-irritating properties.

The flexible member 16 is inserted with the nasogastric tube 14 along a first nostril 9 of a patient to a position where the first fixation point 1 is distal to the posterior nasal septum 10. The flexible member 16 further comprises a magnet 2 provided posterior to the first fixation point 1. The magnet 2 is accommodated within a recess 30 provided within the nasogastric tube 14 to reduce the amount of space required by the magnet 2. A retrieving member 5 is provided having a magnet 6 at the distal tip thereof. The retrieving member 5 is inserted into a second nostril 8 of the patient and passed along the nostril 8 to a point substantially adjacent or distal to the posterior nasal septum 10 wherein the magnets 2, 6 couple and are held together by magnetic force. The retrieving member 5 is then used to draw the second end 3 of the flexible member 16 through the patient's second nostril 8 and to a position external to the patient's nose. The second end 3 of the flexible member 16 is then secured to the nasogastric tube 14 by means of a clamp, adhesive tape or other securing means 20. The retrieving member 5 is sized such that it can be inserted within a patient's nostril 8.

In one embodiment, it is preferred that the nasogastric tube comprises a depression 31 extending along a longitudinal length of the tube proximal to the first fixation point 1, wherein in use, the depression 31 accommodates the tether 16.

The transnasal tube assembly 12 advantageously operates to secure a nasogastric tube 14 in a desired position relative to a patient's nose, allowing minimal movement of the tube, without requiring attachment of the tube to the face of the patient. Advantageously, the tube assembly 12 is held securely in place and cannot be inadvertently removed by movement of the patient.

The magnet 2 on the integrated tether 16 and the magnet 6 on the retrieving member 5 are sized to be insertable into a patient's nostrils 9, 8. Typically, the magnets 2, 6 comprise a ferromagnetic material. In one embodiment, the magnets 2, 6 may comprise permanent magnets, or combinations of permanent magnets and ferromagnetic material. The magnets comprise a material which provides adequate force to effect the coupling of the magnets within the nostril or nasopharynx of a patient, and to enable both magnets, when magnetically coupled together, to be pulled from the patient's nostril. The magnet 2 provided on the tether 16 is placed into close proximity with the magnet 6 provided on the retrieving member 5 such that the magnets couple by magnetic force.

Figure 1:
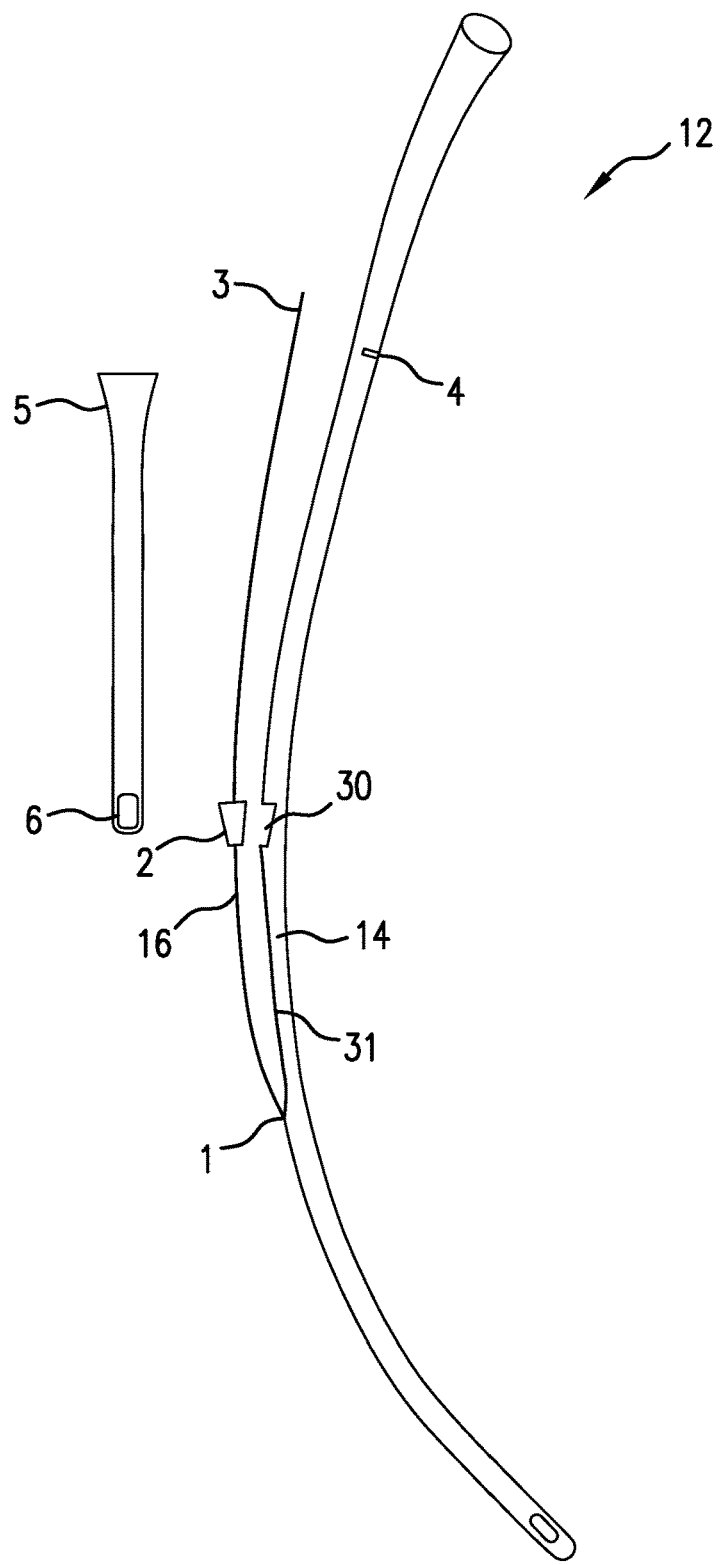
FIG. 1 is a schematic view of a transnasal tube assembly and a retrieving member according to the invention.

In a preferred embodiment, the transnasal tube assembly 12 comprises a flexible member 16 that is integrated permanently into a nasogastric or feeding tube 14 at the internal fixation point 1 seen in FIG. 1. The flexible member 16 is approximately 20 cm long with a magnet 2 attached or incorporated into the flexible member at about 8 cm from the permanent fixation point 1 and about 12 cm from the free end 3 of the flexible member 16. Placement of the nasogastric tube 14 is to a distance such that the magnet 2 of the flexible member 16 is judged to be just distal to the posterior nasal septum 10 as indicated by a marking 4 positioned at approximately 8 cm proximal to the magnet 2 on the flexible member 16 and/or tube 14. The flexible member 16 can be pulled taught at the free end 3 (see FIG. 2) and the tube 14 and flexible member 16 are arranged such that the magnet 2 is medial on the tube 14. The retrieving member 5 is approximately 8 cm long and has a magnet 6 on the distal end and placed down the other nostril. The magnets 2, 6 engage and movement can be felt in the flexible member 16 as the retrieving member 5 is manipulated.

The flexible member 16 is released and the nasogastric tube 14 and the retrieving member 5 are pulled back through respective nostrils 9 and 8 (see FIG. 3). The flexible member 16 pulls back into the tube nostril 9 and is pulled through the contra-lateral retrieving member nostril 8 as the tube 14 and retrieving member 5 are pulled back.

When the retrieving member 5 is fully removed from the nostril, the joined and/or interacting magnets 2, 6 are pulled apart outside of the nose and the totality of the flexible member 16 is pulled through the contra-lateral nostril 8. An external fixation point 7 is created by taping or clamping the tube 14 to the flexible member 16 (see FIG. 4). The remaining flexible member 16 at the free end 3 can be cut or wrapped around the tube 14 and taped.

The nasogastric tube 14 is secure unless the user wishes to remove it and the external fixation point 7 is detached or the flexible member 16 is cut.

A plurality of variations in the above measurements are possible, but the tube 14 distal to the internal fixation point 1 must be of a length judged by the clinician to be appropriate to the clinical needs normally reaching the stomach, the magnet 2 on or in the flexible member 16 must be at a distance to the internal fixation point 1 that is longer than the estimated length of the patient septum 10 and the length from the magnet 2 to the free end 3 of the flexible member 16 must be longer than the estimated length of the patient septum 10.

The size of the patient determines the distance from the posterior nasal septum 10 to the stomach or oesophagus and clinicians will wish to choose the length of the tube for a particular patient. A long tube could for example be about 60 cm beyond the internal fixation point 1 distally, a medium tube could be about 50 cm beyond the internal fixation point 1 and a short tube about 40 cm beyond the internal fixation point 1. One embodiment is a tube which can be cut to a preferred length by the clinician. Paediatric sizes would include shorter lengths. These measurements are indicative and other measurements are possible.

The invention has a permanent attachment of the flexible member 16 to a feeding tube 14 hereby reducing the number of parts from four common as in current bridle systems (i.e. which typically include a flexible member, a retrieving member, a clamp and a feeding or nasogastric tube) to two or three (i.e. a feeding or gastric tube with an integral flexible fixation member and a retrieving member 5 with or without a clamp for the external connection of the free end 3 of the flexible fixation member 16 and the nasogastric tube 14 outside of the patient). Without a clamp, the external fixation point 7 can be simply taped with adhesive tape. The function becomes fundamentally better as there are two fixation points onto the nasogastric tube 14. The tube 14 therefore cannot be removed by hooking a finger into a nostril beyond the bridle fixation.

This means that after fixation there is a fixation point 1 at the posterior nasal septum 10 or deeper rather than at the external nose thereby preventing the problems described above.

Preferably, the transnasal tube assembly is a modification of a nasogastric, nasojejunal, oesophageal or feeding tube with a proximal end disposed, in use, outside the patient and a distal end disposed, in use, inside the patient, comprising an integrated fixation mechanism comprising: a flexible member with a permanent internal fixation point at the distal end of the tube which when in use is near to the posterior nasal septum or deeper within the patients pharynx or oesophagus; and a portion or proximal end of the flexible member designed to form an external fixation point to the tube, in use, substantially outside of the nose and substantially outside the patient.

Preferably, the transnasal assembly integrates a nasogastric tube with a bridle and creates two fixation points on the correctly positioned nasogastric tube. Preferably, one fixation point is permanent and near or adjacent to the posterior nasal septum or deeper within the patient's pharynx or oesophagus (referred to as the internal fixation point) and one is provided outside of the nose (referred to as the external fixation point). Typically, the nasogastric tube has a proximal end which is disposed, in use, outside the patient and a distal end which is normally disposed, in use, in the patient's stomach or oesophagus.

With reference to the drawings, there is also provided a method of anchoring a transnasal tube 14 comprising the transnasal tube assembly 12 of the first aspect, the method comprising the steps of: (i) inserting the transnasal tube assembly 12 along a first nostril 9 of a patient to a position wherein the first fixation point 1 of the integrated tether 16 is distal to the posterior nasal septum 10; (ii) inserting a retrieving member 5 into a second nostril 8 and using the retrieving member 5 to draw the second end 3 of the integrated tether 16 through the second nostril 8 to a position outside the patient; and (iii) securing the transnasal tube 14 and tether 16 together at a second fixation point 7 outside of the patient.

FIG. 1 shows an embodiment of the invention with the tube 14 and the flexible member 16 permanently attached at 1, with a free end 3 and a magnet 2. The more rigid retrieving member 5 has a proximal end which may be held by an operator (e.g. a medical professional) and a distal end with a magnet 6 to engage the magnet 2 beyond the posterior nasal septum 10 during placement.

Figure 2:
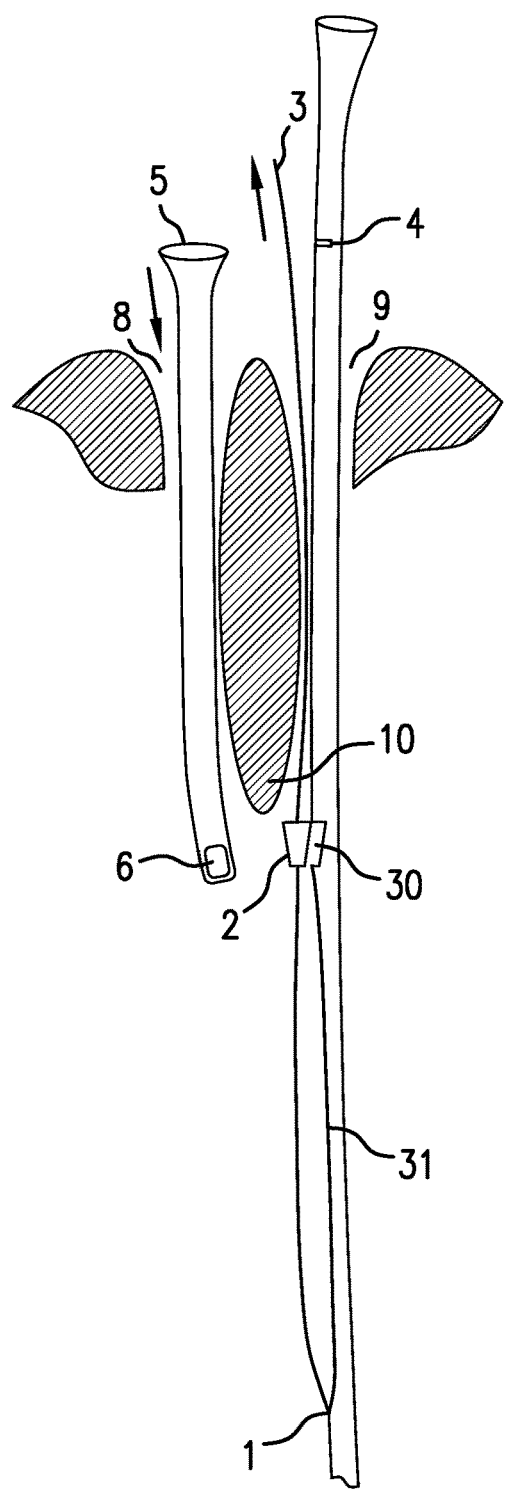
FIG. 2 is a schematic view of the transnasal tube assembly and retrieving member according to the invention when inserted into first and second nostrils of a patient.

FIG. 2 shows an embodiment of the invention wherein the transnasal tube assembly 12 is inserted in the patient's nostril 9. The free end 3 of the flexible member 16 is pulled taught and a retrieving member 5 is placed into the contra-lateral nostril 8. The magnets of these members 6 and 2 attach at a position distal to the nasal septum 10.

FIG. 3 shows an embodiment wherein the tube 14 and the retrieving member 5 are drawn back and the flexible member 16 is pulled through from one nostril 9 through the contra-lateral nostril 8. The free end 3 of the flexible member 16 pulls through the tube nostril 9 and around the nasal septum 10 and up through the contra-lateral nostril 8.

FIG. 4 shows an embodiment wherein the flexible member 16 is taped or clamped to form an external fixation point 7 and an internal fixation point 1.

With reference to the drawings, there is also provided a kit comprising the transnasal tube assembly 12 of the first aspect, further comprising a retrieving member 5.

The invention claimed is:

1. A transnasal tube assembly, comprising: a transnasal tube; and an integrated tether for anchoring the transnasal tube, wherein the integrated tether further comprises a retrieving means, wherein the retrieving means comprises a magnet, wherein the integrated tether is permanently fixed to the transnasal tube at a first fixation point, wherein the integrated tether is configured to be reversibly fixable to the transnasal tube at a second fixation point, wherein the integrated tether comprises a first end and a second end, wherein the first end is provided at the first fixation point and the second end is proximate to the second fixation point, and wherein, when the transnasal assembly is disposed adjacent to a posterior nasal septum of a patient, the first end of the integrated tether is secured to the transnasal tube at a position distal to the posterior nasal septum and the second end of the integrated tether is secured to the transnasal tube at a position external to the patient.

2. The transnasal tube assembly of claim 1, wherein the transnasal tube comprises a recess to accommodate the magnet.

3. The transnasal tube assembly of claim 1, further comprising a clamp to secure the transnasal tube and the integrated tether at the second fixation point.

4. The transnasal tube assembly of claim 1, wherein the transnasal tube comprises a depression along a longitudinal length of the transnasal tube proximal to the first fixation point, wherein the depression accommodates the integrated tether.

5. The transnasal tube assembly of claim 1, wherein the integrated tether comprises a flexible member.

6. The transnasal tube assembly of claim 5, wherein the flexible member is elongate.

7. The transnasal tube assembly of claim 1, wherein the transnasal tube comprises a nasogastric tube, a nasojejunal tube, an oesophageal tube or a feeding tube.

8. The transnasal tube assembly of claim 7, further comprising adhesive tape to secure the nasogastric tube and the integrated tether at the second fixation point.

9. The transnasal tube assembly of claim 7, further comprising indication means to indicate the position of the nasogastric tube and/or the integrated tether when inserted within a nostril of a patient.

10. The transnasal tube assembly of claim 9, wherein the indication means comprises a marker.

11. The transnasal tube assembly of claim 1, further comprising a retrieving member.

12. The transnasal tube assembly of claim 11, wherein the retrieving member comprises an introducing stylet, a wire or other intra-luminal member.

13. The transnasal tube assembly of claim 11, wherein the retrieving member comprises a magnet.

14. The transnasal tube assembly of claim 13, wherein the magnet is provided at the distal end of the retrieving member.

15. The transnasal tube assembly according to claim 11, wherein, the retrieving member is configured to engage a retrieving means provided on the integrated tether and wherein the retrieving member is configured to pull a second end of the integrated tether to a position exterior to a nostril of the patient.

16. The transnasal tube assembly of claim 15, wherein, in use, the first fixation point is provided at a position distal to a posterior nasal septum of the patient and the second fixation point is provided at a position exterior to the nostril of the patient.

17. A kit comprising the transnasal tube assembly of claim 1, further comprising a retrieving member.

18. The kit of claim 17, wherein the retrieving member comprises a magnet at a distal end thereof.

19. The kit of claim 17, further comprising a clamp and/or adhesive tape for securing the transnasal tube and the integrated tether at the second fixation point.

20. A method of anchoring a transnasal tube comprising the transnasal tube comprising the transnasal tube assembly of claim 1, the method comprising the steps of:
   (i) inserting the transnasal tube assembly along a first nostril of a patient to a position wherein the first fixation point of the integrated tether is distal to a posterior nasal septum;
   (ii) inserting a retrieving member into a second nostril and using the retrieving member to draw the second end of the integrated tether through the second nostril to a position outside the patient; and
   (iii) securing the transnasal tube and the integrated tether together at a second fixation point outside of the patient.

21. The method of claim 20, wherein step (ii) comprises the use of a magnet provided at a distal end of the retrieving member and a magnet provided on the integrated tether to draw the second end of the tether out of the second nostril of the patient.

22. The method of claim 20, wherein step (iii) comprises the use of a clamp and/or adhesive tape.

23. The method of claim 20, wherein the position of the transnasal tube and the integrated tether is monitored using indication means.

* * * * *